United States Patent
Hong

(10) Patent No.: US 10,640,434 B2
(45) Date of Patent: May 5, 2020

(54) PROCESS AND APPARATUS FOR PRODUCING OLEFINS FROM LIGHT ALKANES

(71) Applicant: Kainos Tech Incorporated, Crown Point, IN (US)

(72) Inventor: Jin Ki Hong, Cypress, CA (US)

(73) Assignee: KAINOS TECH INCORPORATED, Crown Point, IN (US)

( * ) Notice: Subject to any disclaimer, the term of this patent is extended or adjusted under 35 U.S.C. 154(b) by 0 days.

(21) Appl. No.: 16/027,432

(22) Filed: Jul. 5, 2018

(65) Prior Publication Data

US 2019/0010098 A1     Jan. 10, 2019

Related U.S. Application Data

(60) Provisional application No. 62/604,421, filed on Jul. 6, 2017.

(51) Int. Cl.
| | |
|---|---|
| *C07C 5/333* | (2006.01) |
| *B01J 8/00* | (2006.01) |
| *B01J 8/18* | (2006.01) |
| *B01J 8/26* | (2006.01) |
| *B01J 8/24* | (2006.01) |

(52) U.S. Cl.
CPC ............ *C07C 5/333* (2013.01); *B01J 8/0055* (2013.01); *B01J 8/1836* (2013.01); *B01J 8/1872* (2013.01); *B01J 8/24* (2013.01); *B01J 8/26* (2013.01); *B01J 2208/00991* (2013.01)

(58) Field of Classification Search
CPC ............................... B01J 8/062; B01J 8/1836
See application file for complete search history.

(56) References Cited

U.S. PATENT DOCUMENTS

| | | | |
|---|---|---|---|
| 4,778,942 A * | 10/1988 | Vora ........................ | C07C 5/325 |
| | | | 585/655 |
| 6,392,113 B1 | 5/2002 | Gartside | |
| 7,902,416 B2 | 3/2011 | Glover et al. | |
| 2016/0289141 A1* | 10/2016 | Bachmann ............... | C07C 5/367 |

FOREIGN PATENT DOCUMENTS

| | | | | |
|---|---|---|---|---|
| GB | 1147359 A * | 4/1969 | ............ | B01J 8/1836 |
| WO | WO-2015075124 A1 * | 5/2015 | ............ | C07C 5/367 |
| WO | WO-2016027219 A1 * | 2/2016 | ............ | C07C 5/3332 |

* cited by examiner

*Primary Examiner* — In Suk C Bullock
*Assistant Examiner* — Alyssa L Cepluch
(74) *Attorney, Agent, or Firm* — STIP Law Group, LLC

(57) ABSTRACT

A process and an apparatus for producing olefins from light alkanes. A light alkane feed is contacted with catalyst particles in each of reactors, wherein each of the reactors is a fluidized bed reactor. At least a portion of the alkane feed is converted to olefins using the catalyst particles, wherein the olefins form a part of a reactor effluent stream. The reactor effluent streams from each of the reactors are merged to form a merged effluent stream. The merged effluent stream is separated into an olefin stream and the other streams. The other streams may comprise a recycle stream and light gases.

15 Claims, 4 Drawing Sheets

PROCESS AND APPARATUS FOR PRODUCING OLEFINS FROM LIGHT ALKANES

CROSS-REFERENCE TO RELATED APPLICATIONS

This application claims the benefit of priority under 35 U.S.C. § 119(e) to U.S. Provisional Patent Application No. 62/604,421, filed on Jul. 6, 2017, which is hereby incorporated by reference in its entirety.

FIELD OF INVENTION

The present invention relates to a process and an apparatus for producing olefin from a C3-C4 alkane feed.

BACKGROUND OF THE INVENTION

Catalytic dehydrogenation is an industrial process that produces C3-C4 range olefins such as propylene, butenes (1-butene, 2-butene, or isobutene), and 1,3-butadiene from its corresponding light alkane feed. The light alkane feed comprises propane, butane, or a combination thereof. A stable supply of light alkane feedstock at competitive prices makes dehydrogenation a preferred process for C3-C4 olefin production compared to other production processes such as steam cracking of naphtha or fluid catalytic cracking (FCC) of heavy-portion of crude oil.

Light alkane dehydrogenation is an equilibrium-limited and highly endothermic reaction. Equilibrium conversion of light alkane feed increases with temperature and decreases with pressure. Cracking and coking reactions, promoted by elevated temperature as side reactions, reduce the selectivity toward the desired olefins.

Light alkane dehydrogenation is a strongly endothermic reaction and, therefore, the process for producing its corresponding olefin from the light alkane feed requires supplying a large quantity of reaction heat to achieve industrially attractive production rates. Approximately 2,952 kJ of thermal energy is required for the reaction heat per kg of propylene produced from propane. Considering this strong endothermic requirement, there is a need for a reliable and efficient method and apparatus for providing the reaction heat required for producing olefins from the light alkanes at industrially attractive production rates.

The present invention found that another important factor in olefins production is uniform catalyst bed temperature in a specific temperature range. Findings of the present invention suggest that light alkane conversion for olefin production is highly sensitive to reaction temperature in terms of light alkane conversion rates and catalyst deactivation. If the catalyst bed temperature is below 500° C., light alkane conversion rate is too low to meet commercially attractive production rates. On the other hand, unacceptably fast catalyst deactivation is driven at catalyst bed temperatures higher than 700° C., and this leads to olefin production cycle times between catalyst regenerations that are too short for commercial operation. Achieving a uniform catalyst bed temperature in a desired temperature range, preferably between 500° C. and 700° C., more preferably between 520° C. and 680° C., and most preferably between 540° C. and 660° C., in industrial scale reactors is critical for commercial viability of olefin production from light alkanes.

Methods for supplying reaction heat have been developed by chemical industry for reactions of endothermic nature. However, adoption of these methods for dehydrogenation of light alkanes yields undesirable operational issues and non-uniform temperature distributions in the catalyst bed. For instance, preheating the light alkane feedstock to provide sufficient sensible heat for the endothermic reaction is not feasible because the reaction heat required for industrially attractive rates is substantially larger than the quantity of sensible heat achievable through light alkane feedstock preheating. Excessive preheating of the feedstock in order to increase sensible heat and provide the reaction heat required often leads to technical issues, including thermal breakdown of feedstock, accelerated catalyst deactivation, and shortened lifetime of preheating tubes. Heating an inter-stage stream for the next stage reactor in serially connected multi-stage reactors configuration is not desirable either because heating of the inter-stage stream leads to thermal breakdown of the desired product at elevated temperatures and its resultant building-up of coke inside the tube.

Intensive heating-up of external surfaces of fixed bed reactors would not be applicable. Catalyst beds with a fixed position in a stationary state inside an externally heated reactor impede heat supply itself and create non-uniform temperature distributions within the catalyst bed. This leads to accelerated catalyst coking and catalyst sintering problems near the reactor wall and not enough thermal energy to drive the endothermic reaction in the center of the catalyst bed.

Catalyst heating by burning coke while regenerating catalyst (and burning extra fuel when needed) and recycling the heated catalyst for reaction heat supply has been explored. Even though circulation of heated catalyst particles from the catalyst regenerator for reaction heat supply has been commercially employed in fluid catalytic cracking (FCC) for heavy portions of crude oil, the same approach or its modified approach (e.g., back-mixing of the regenerated catalyst particles) would not work properly with light alkanes as feedstock. Light alkane conversion for the production of olefins requires substantially larger amounts of reaction heat than cracking of heavy portions of crude oil when compared on a per unit feedstock mass basis. The present invention also found that light alkane feed produces coke at substantially lower yields than FCC methods for heavy portions of crude oil. The much stronger endothermic requirement of light alkane dehydrogenation combined with substantially lower coke yield in the reaction makes it impractical to use coke as source of reaction heat supply.

Catalyst deactivation driven by coke formation is another technical hurdle in olefin production from light alkanes. Formation of coke over or within the catalyst structure progresses over the course of olefin production, leading to a gradual drop in olefin production rates. Regeneration of deactivated catalysts makes it difficult or impossible to produce olefins from a reactor in a continuous manner and to operate downstream separation systems or units without interruption.

Taken together, there is a need for a new process and apparatus for producing olefins from a light alkane feedstock by developing a reliable and efficient reaction heat supply to the reactor with a uniform catalyst bed temperature in a desired temperature range and by making the entire process continuous.

SUMMARY OF THE INVENTION

A new process and apparatus for producing olefins from light alkanes is provided. The process comprises contacting a light alkane feed with dehydrogenation catalyst particles in each reactor. The process discloses that each of the reactors is a fluidized bed reactor partially embedded in a furnace; converting at least a portion of the alkane feed to olefins using the catalyst particles, wherein the olefins form a part of reactor effluent streams; merging the reactor effluent streams from each of the reactors to form a merged effluent stream; and separating an olefins stream comprising the olefins from the merged effluent stream. The separating step may separate the merged effluent stream into the olefin steam, a recycle stream, and light gases. The light alkane feed may comprise propane, n-butane, isobutane, or a combination thereof. The olefins stream may comprise propylene, 1-butene, 2-butene, isobutene, 1,3-butadiene, or a combination thereof. The recycle stream may comprise propane, n-butane, isobutane or a combination thereof. The light gases may comprise methane and hydrogen. In each of the reactors, the catalyst particles are fluidized. The catalyst particles may be 10-500 micrometers in diameter.

In the converting step, an outside wall of each of the reactors is heated by a flue gas, wherein the flue gas is generated by combustion of a gaseous fuel or a liquid fuel. The pressure of the reactor is 100 psig (790 kPa) or less during the converting step. The temperature of the catalyst particles is between 500° C. and 700° C. during the converting step. An upper end portion of each of the reactors is protruded from an upper wall of the furnace, wherein the protruded portion is 10%-70% of the length of each of the reactors in a height direction.

The process may further comprise a step of regenerating the catalyst particles to reactivate the catalyst particles deactivated during the converting step, wherein the reactors are fluidly disconnected from the light alkane feed and fed with a gas stream. The gas stream may comprise either air or hydrogen during the regenerating step. All the reactors in a furnace are switched as a group between in a production mode for producing olefins and in a regeneration mode for regenerating catalysts deactivated during the production mode.

In one embodiment, the furnace comprises multiple furnaces, and the first merged effluent stream from each of the multiple furnaces is further merged with each other to form a second merged effluent stream. The process may comprise a step of regenerating the catalyst particles to reactivate the catalyst particles deactivated during the converting step, wherein all the reactors in the furnace in which the regenerating step occurs are fluidly disconnected from the light alkane feed and fed with a gas stream. The gas stream may comprise either air or hydrogen, or a combination thereof, during the regenerating step. All the reactors in the furnace in which the regenerating step occurs are fluidly disconnected from the second merged effluent stream.

DETAILED DESCRIPTION OF THE INVENTION

Figure 1:
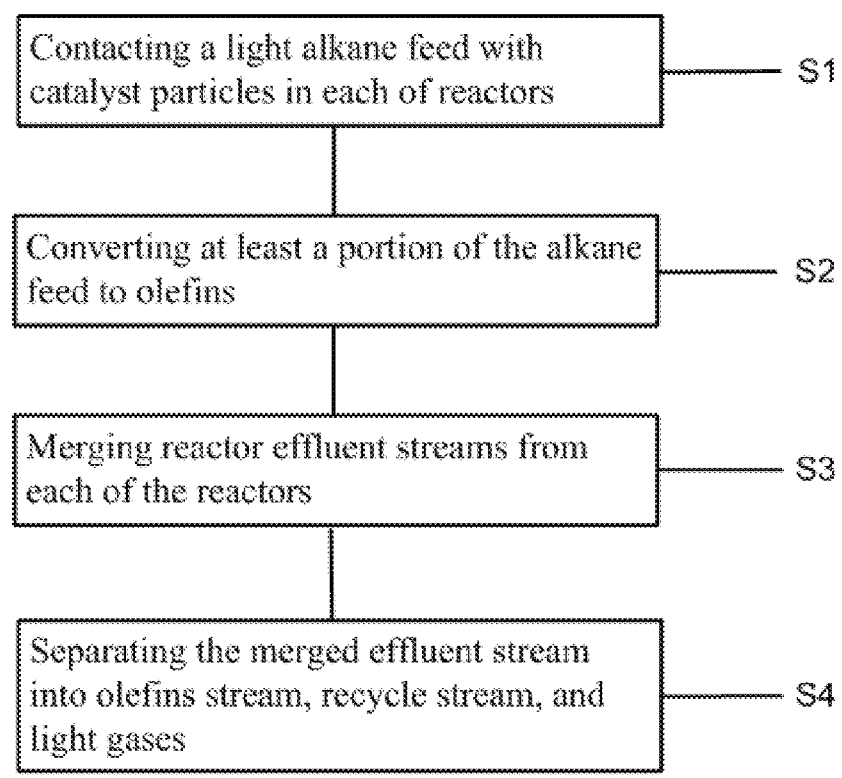
FIG. 1 shows the steps of producing olefins from a light alkane feed.

FIG. 1 shows a process for producing olefins which comprises contacting a light alkane feed with catalyst particles in each of the reactors (S1), converting at least a portion of the alkane feed to an olefin or olefins (S2), merging reactor effluent streams from each of the reactors (S3), and separating the merged effluent stream into an olefin stream and the other streams. The other streams may comprise a recycle stream and light gases (S4). The light alkane feedstock comprises propane, butanes (n-butane, isobutane), or a combination thereof. Light alkane is also referred to as lower alkane or light or lower paraffin.

Figure 2:
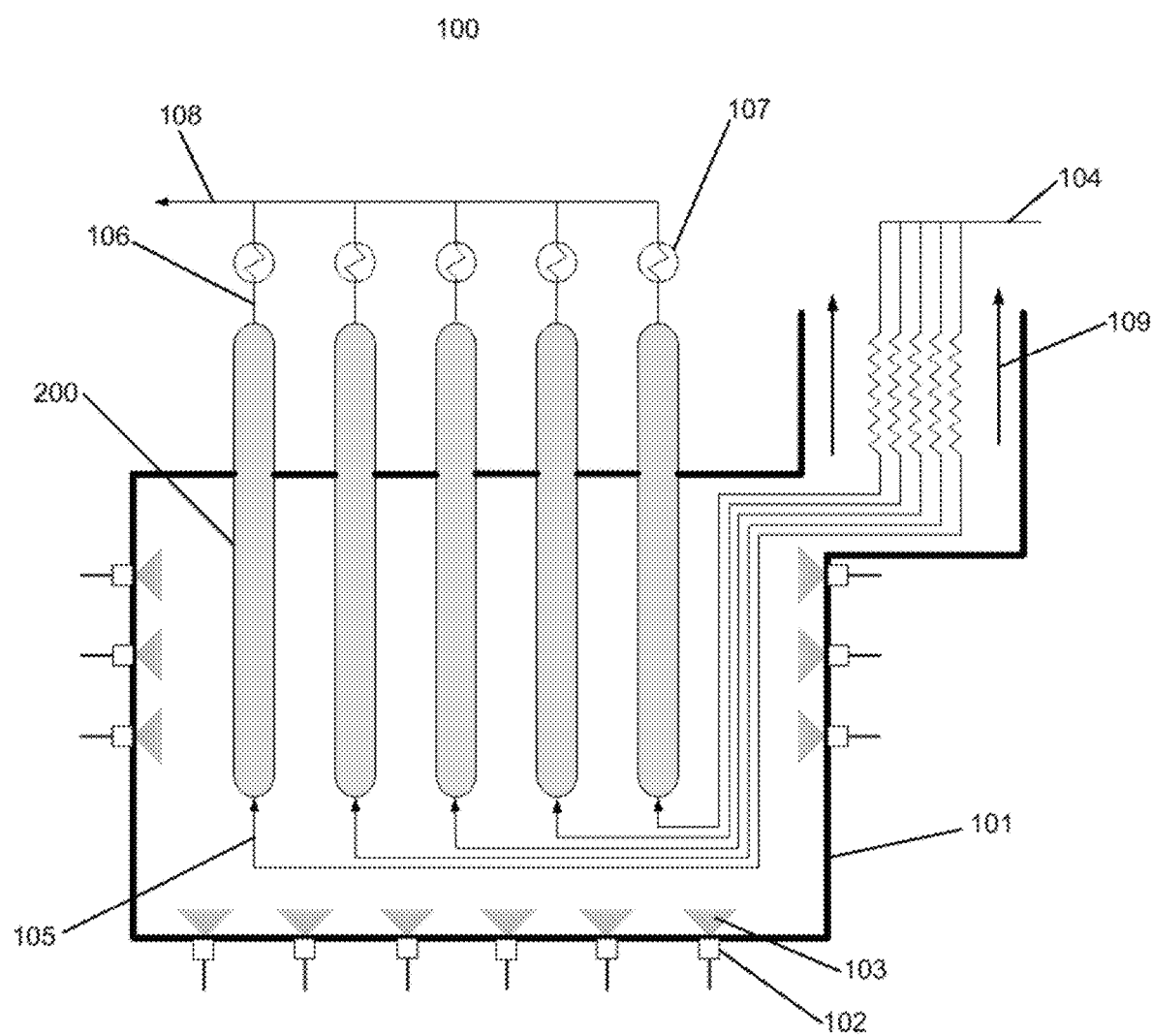
FIG. 2 is a simplified schematic diagram of a furnace of the present invention.

FIG. 2 shows a simplified schematic diagram of a furnace 100 with a furnace wall 101 of the present invention in which multiple reactors 200 are heated by flue gas for olefin production. The reactors are vertically mounted fluidized bed reactors and are partially embedded in a furnace 100. The reactors are arranged in parallel, and not in series. The number of reactors in the furnace is determined based on target olefin production rates from reactors in a furnace and production rates of individual reactors. An upper end portion of each of the reactors is protruded from an upper wall of the furnace, wherein the protruded portion is 10%-70% of the length of each of the reactors in a height direction. Burners 102 are installed on an inner wall area of the furnace as follows: a ceiling area, a side wall area, and/or a floor area. The burners produce a flue gas 103 by combusting a gaseous or a liquid fuel. The burners 102 are positioned in such a way that promotes uniform distribution of thermal energy by the flue gas flow inside the furnace and avoids formation of hot spots on the reactor wall. The light alkane feed 104 is split into multiple streams 105, each of which is fed into its corresponding reactor. Reactor effluent 106 is quenched through a heat exchanger 107. The heat exchanger generates a steam at an elevated pressure (not shown in the diagram) and the steam can be used to meet the process energy requirements. After the heat exchanger 107, reactor effluents 106 from individual reactors are merged to become a first merged effluent stream 108. In one embodiment, quenching of the reactor effluent using a heat exchanger can be done after the reactor effluents are merged.

The furnace temperature or flue gas temperature inside the furnace is preferably between 700° C. and 1200° C., more preferably between 750° C. and 1150° C., and most preferably between 800° C. and 1100° C., providing temperature gradients high enough for the heat supply needed for olefin production during the converting step at industrially attractive rates. Flue gas flowing around the outer walls of the reactors in a forced convection mechanism promotes heat transfer from the flue gas to the outer walls of the reactor. Heat transfer through radiation also occurs along with the convective heat transfer. A heat transfer coefficient higher than 200 W/m$^2$-K is achievable and this realizes olefin production at industrially attractive rates. Flue gas before exiting the furnace 109 provides thermal energy for preheating the light alkane feed into the individual reactors and improves efficiency of the process. To do so, at least a portion of the multiple streams 105 are placed inside the furnace. In order to improve heat exchange from the flue gas to the light alkane feed stream, tubing for the light alkane feed may be manufactured in the form of coils or other shapes so that the contact between the flue gas and the tubing wall is increased.

The fluidized bed reactors in a furnace are switched as a group between in a production mode for producing olefins and in a regeneration mode for regenerating catalysts deactivated during the production mode. All the reactors in a furnace are switched to the regeneration mode as a group when olefin production rates drop below a predetermined rate. Formation of coke over or within the catalyst structure progresses over the course of olefin production and this leads to the gradual drop in the olefin production rates. Controlled coke burning using air or coke conversion to methane gas by reaction with hydrogen proceeds as the light alkane feed is switched to air or hydrogen flow. When catalyst regeneration is completed, the reactors are switched back to light alkane feed for olefin production mode operation. Purging of the reactors with inert gas, such as nitrogen, may be performed before switching the reactors from production mode to regeneration mode, and from regeneration mode to production mode. This avoids occurrence of undesirable reactions, such as combustion of hydrocarbons, and its resultant negative effects on catalyst performance.

Catalyst regenerations through coke burning using air or coke conversion to methane using hydrogen are exothermic reactions. In a furnace, if the exothermic catalyst regeneration is to occur in some reactors, while the other reactors are producing olefins at the same time, then the catalyst particles in reactors of catalyst regeneration mode operation would reach 800° C. or even higher. Reaching this unacceptably high temperature would lead to thermal degradation of catalyst particles and its resultant catalyst activity loss and drop in olefin production rates. Therefore, concurrent olefin production in some reactors and catalyst regeneration in the other reactors in the same furnace needs to be avoided. In other words, olefin production in some reactors and catalyst regeneration in the other reactors do not occur concurrently in the same furnace. Arrangement of reactors in parallel as disclosed in the present invention prevents olefin production in some reactors and catalyst regeneration in the other reactors from occurring at the same time in the same furnace.

Figure 3:
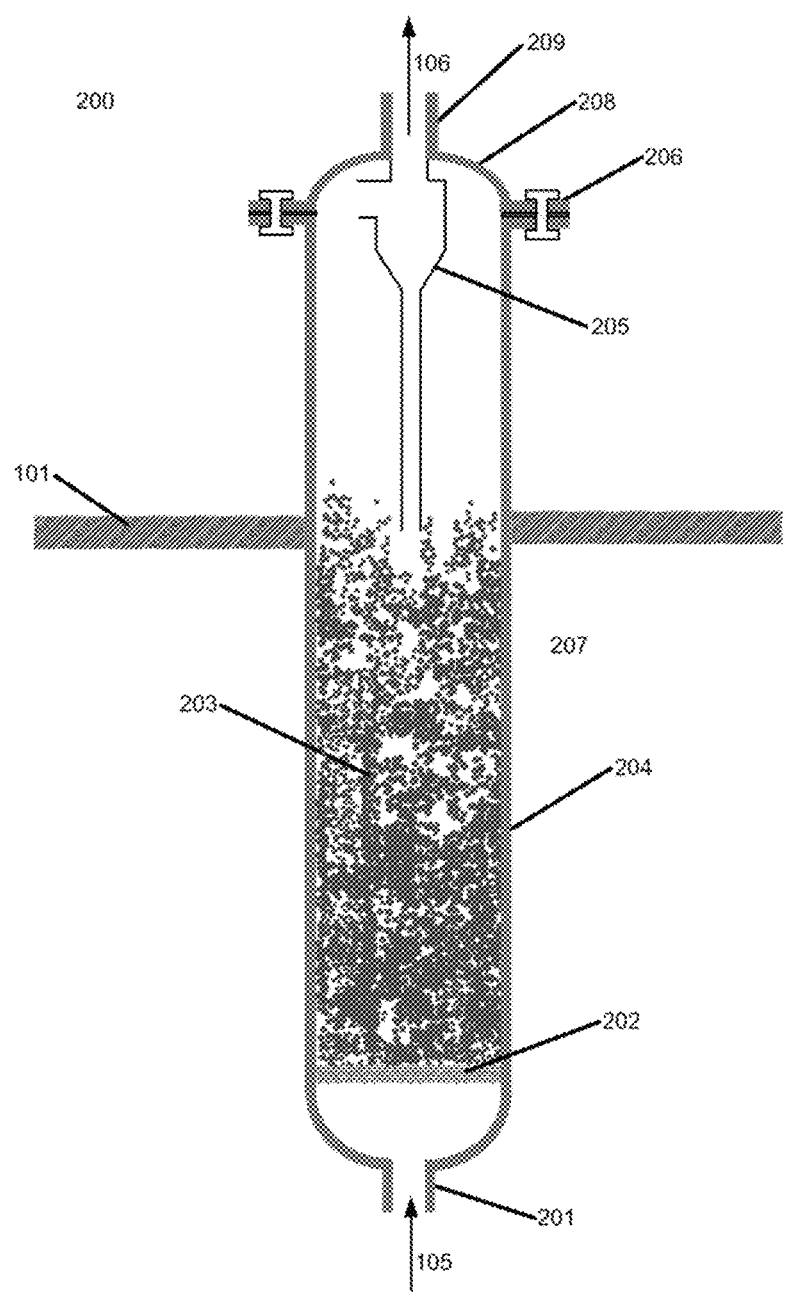
FIG. 3 is a simplified schematic diagram of a fluidized bed reactor of the present invention.

FIG. 3 shows a simplified schematic diagram of a fluidized bed reactor (cross-sectional view) of the present invention. The light alkane feed into the individual reactor enters a fluidized bed reactor 200 through a reactor feed inlet 201. The fluidization plate 202 promotes fluidization of catalyst particles (or bed) 203. The catalyst particles comprise dehydrogenation catalyst and binder material. The dehydrogenation catalyst may further comprise noble metal, non-noble metal, or a combination thereof. Examples include Pt-based catalysts and chromia-based catalysts. The binder material holds individual catalyst powders together to make a spherical shape of controlled particle sizes and improves mechanical strength or attrition resistance of the catalyst particles. The binder material is mixed with dehydrogenation catalyst powders before being transferred to spray drying or other mechanical operations for particle formation. The finished catalyst particles are 10-500 micrometers (or microns) in diameter. The fluidization plate 202 may take the form of a porous metal plate/disk, bubble cap plates, or spargers. The gas flow rate is regulated for fluidization regimes of either bubbling or turbulent fluidization, or in between the two. Flow rates lower than dense bed transition velocity or higher than transport velocity is not desirable for the present invention.

Thermal energy is transferred from the flue gas to the catalyst particles (or bed) 203 and the gas flow inside the reactor vessel 207 through the reactor wall 204. An upper end portion of each of the reactors is protruded from an upper wall of the furnace, wherein the protruded portion is 10%-70% of the length of the reactors in a height direction. The length of the reactor is defined as the length between the uppermost part of a reactor feed inlet 201 and the lowermost part of a reactor effluent outlet 209. The protruded portion is adjusted so that a reactor portion corresponding to the fluidized catalyst bed is heated by the flue gas inside the furnace, while heating of a reactor portion above the catalyst bed is avoided to minimize thermal breakdown of hydrocarbons.

A cyclone with dipleg 205 separates catalyst particles from gas stream leaving the reactor and returns them to the reactor vessel 207. This minimizes or avoids entrainment of the catalyst particles 203 out of the reactor 200. Multiple cyclones may be connected in series for improved separation of catalyst particles. The cyclone may be installed either internally or externally to the reactor 200. A flange connection 206 provides gas tight mechanical seal between the reactor vessel 207 and the reactor vessel cover 208. A reactor effluent 106 leaves the reactor 200 through a reactor effluent outlet 209.

Upward flow of the light alkane feed inside the reactor drives fluidization of the catalyst particles and promotes heat transfer from the inner surface of the reactor wall to the catalyst particles and gas flow inside the reactor. Driven by the fluid-like behavior of the catalyst particles, a heat transfer coefficient as high as 600 W/m$^2$-K is readily achievable compared to less than 100 W/m$^2$-K in non-fluidized heat transfer cases. The high thermal mass or heat capacity of the catalyst particles impinging the inner surface of the reactor wall of the fluidized bed reactor at a high frequency substantially improves heat transfer to the catalyst particles and gas flow inside the reactor. A uniform catalyst bed temperature is realized, which is attributable to large surface area of catalyst particles circulating within the reactor that are in contact with surrounding gas flow in a random manner.

Traditional heat supply through a fixed catalyst bed is highly limited as the catalyst in stationary position itself impedes heat transfer. As a result, steep temperature gradients develop across the catalyst bed. Excessively hot catalysts near the reactor wall are susceptible to catalyst deactivation and thermal degradation, while catalysts located away from the reactor wall lack thermal energy and are unable to drive endothermic reactions.

FCC-type heat supply through coke burning in deactivated catalyst particles and circulation of the heated catalyst particles is not suitable for light alkane conversion because coke yield in light alkane conversion is too low to meet the reaction heat required for industrially attractive olefin production rates. Light alkane dehydrogenation for olefin production requires much larger reaction heats than scission of carbon-carbon bond in cracking of heavy portions of crude oil in an externally circulating fluidization system. Compared to 5 mole % or higher coke yield obtainable in catalytic cracking of heavy portions of crude oil in an externally circulating fluidization system, light alkane conversion to olefins produces less than 1 mole % of coke yield. This low yield of coke cannot provide sufficient reaction heat through coke burning for industrially attractive conversion rates in an externally circulating fluidization system or its modified systems. Burning additional fuel in order to elevate catalyst particle temperatures would lead to thermal degradation of catalyst particles and loss in catalytic activity.

The reactor wall material of the present invention is comprised of alloy metals that exhibit high thermal conductivity. Thermal conductivities higher than 20 W/m-K of the alloy metals have proven effective for heat transfer in high temperature chemical processes such as steam crackers for olefin production and steam methane reformers for synthesis gas production. Heat flux higher than 30 kW/m² is achievable through the reactor wall made of the alloy metals.

Catalyst bed temperatures are preferably maintained between 500° C. and 700° C., more preferably between 520° C. and 680° C., and most preferably between 540° C. and 660° C. for olefins production. Above 700° C., catalyst deactivation driven by coking progresses rapidly and this shortens the olefin production cycle time between catalyst regenerations. Below 500° C., the olefins production rate is too low to meet industrially attractive production rates. The reactor pressure is 100 psig (790 kPa) or less, preferably between 0 psig (101 kPa) and 80 psig (653 kPa).

Enabled by using fluidized bed reactors arranged in parallel inside a furnace, the present invention provides an effective supply of thermal energy to the reactors while achieving a uniform catalyst bed temperature inside the reactors. Driven by upward flow of feedstock, catalyst particles are fluidized and internally circulated inside the reactor. The fluidized bed reactors are partially embedded inside or surrounded by a furnace where the flue gas from combustion of gaseous or liquid fuel provides thermal energy to the catalyst particles and gas flow inside the reactor through the reactor wall.

Figure 4:
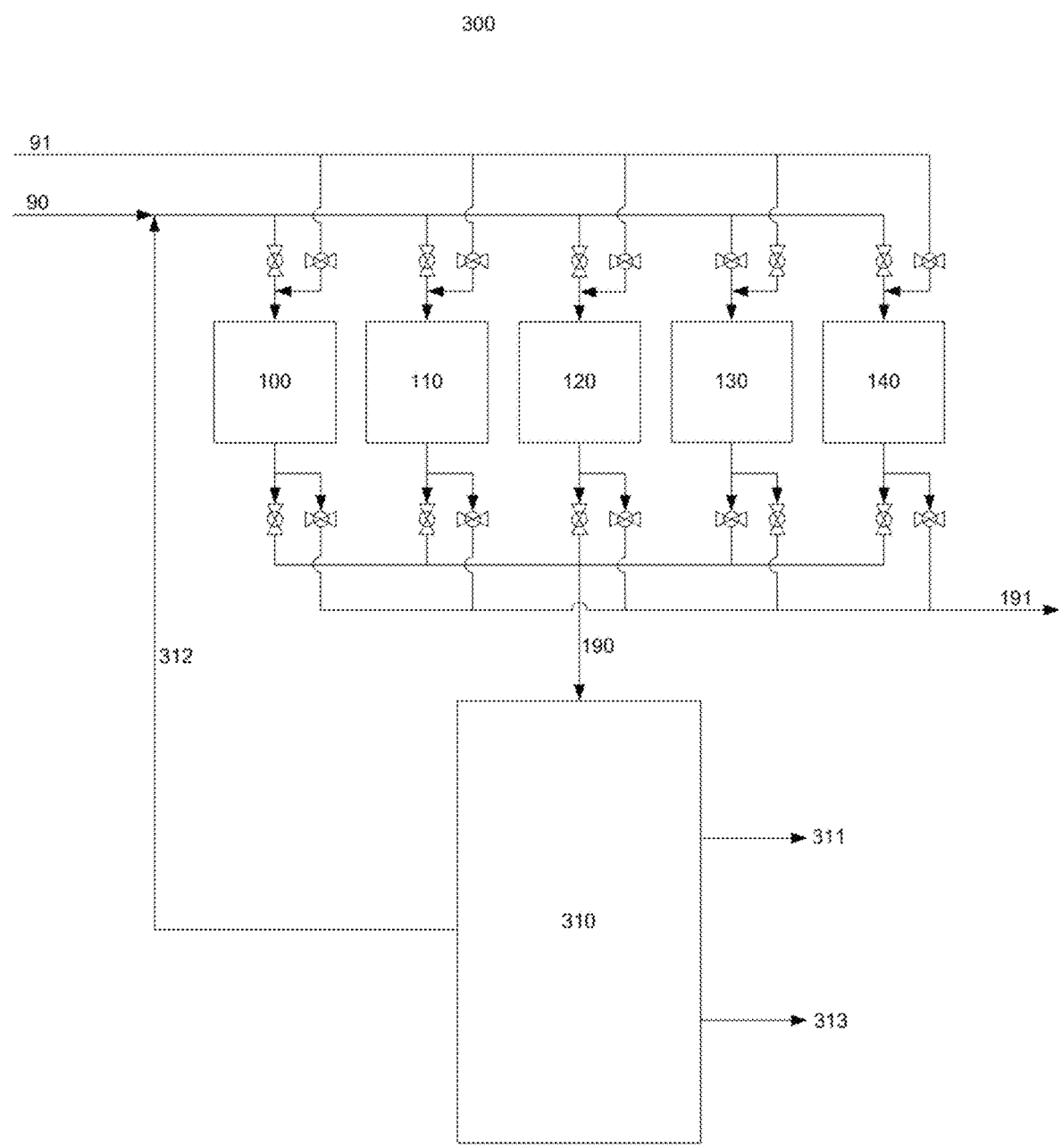
FIG. 4 is a simplified schematic diagram of the present invention in which olefins-containing reactor effluent streams from multiple furnaces are integrated with a downstream separation system while reactors in catalyst regeneration mode operation in the other furnace are fluidly disconnected from the separation system.

FIG. 4 shows a simplified schematic diagram of the present invention in which reactor effluent streams comprising olefins from multiple furnaces are integrated with downstream separation system. An integrated production system 300 comprises multiple furnaces (100, 110, 120, 130, and 140) and separation system 310. The number of furnaces in olefins production mode is determined based on overall olefins production rate target, the number of reactors inside a furnace, and the production rates of individual reactors.

The fluidized bed reactors in a furnace are switched as a group between in a production mode for producing olefins and in a regeneration mode for regenerating catalysts deactivated during the production mode. As an example, all the reactors in furnace 100, 110, 120, and 140 are in a production mode of olefins, while all the reactors in furnace 130 are in a catalyst regeneration mode at one point of system operation. The reactors inside furnace 100, 110, 120, and 140 are fed with light alkane supply 90. The reactors inside the furnace 130 are fluidly disconnected from the reactors in the other furnaces by closing valves for the light alkane feed supply and for merging the merged reactor effluent with those from the other furnaces. The gas stream for catalyst regeneration 91 enters the reactors in furnace 130 for catalyst regeneration. The resultant catalyst regeneration effluent 191 is removed out of the system. Reactors in a furnace are switched as a group between the production mode and the regeneration mode in an orderly manner. Integration of multiple furnaces with the capability of switching operations between in the production mode and in the regeneration mode realizes continuous production of olefins without disrupting operation of the downstream separation system 310.

The first merged effluent streams from the furnaces in the production mode are combined to form a second merged effluent stream 190. The second merged effluent stream 190 enters the downstream separation system 310. The downstream separation system 310 comprises compressors, heat exchangers, cryogenic expanders, and fractionation columns for separation of the second merged effluent stream 190 into multiple streams based on boiling point difference. In one embodiment, the downstream separation system 310 separates the second merged effluent stream 190 into olefin stream 311, recycle stream 312, and light gases 313. The olefin stream 311 comprises propylene, 1-butene, 2-butene, isobutene, 1,3-butadiene, or a combination thereof depending on the light alkane feed. The recycle stream 312, comprised of un-reacted light alkane feed, may be recycled to the reactors of olefins production mode operation after being merged with the light alkane supply 90. The recycle stream 312 may further comprise 1-butene, 2-butene or both in order to increase 1,3-butadiene concentration in the olefin stream 311. Light gases 313, mainly comprising methane and hydrogen, may be used for process energy requirements including flue gas production inside the furnaces.

Improved heat transfer from the hot flue gas to the catalyst particles and gas flow inside a fluidized bed reactor allows olefin production rates as high as or even higher than 10 metric tons/day from a single reactor. The combination of multiples of reactors arranged in parallel in a furnace, switching reactors operation mode as a group in a furnace between olefins production and catalyst regeneration, and use of multiple furnaces in an orderly cyclic manner allows olefin production at commercially attractive production rates and in a continuous manner.

The invention claimed is:

1. A method for producing olefins comprising:
contacting a light alkane with dehydrogenation catalyst particles in at least two reactors, wherein each of the reactors is a fluidized bed reactor partially embedded in a furnace such that an upper end portion of each of the reactors is protruded from an upper wall of the furnace, wherein the light alkane is propane, butane, or a combination thereof;
converting at least a portion of the alkane to olefins, wherein the olefins form a part of a reactor effluent stream, and wherein, during the converting, the catalyst particles reach a level of the upper wall of the furnace;
merging the reactor effluent streams from each of the reactors to form a first merged effluent stream;
separating an olefin stream comprising the olefins from the first merged effluent stream; and
regenerating the catalyst particles to reactivate the catalyst particles deactivated during the converting,
wherein all the reactors in the furnace are switched as a group between a production mode for performing the converting and a regeneration mode for regenerating the catalyst particles deactivated during the production mode.

2. The method of claim 1, wherein the olefin stream comprises propylene, 1-butene, 2-butene, isobutene, 1,3-butadiene, or a combination thereof.

3. The method of claim 1, wherein the separating step separates the first merged effluent stream into the olefin steam, a recycle stream, and light gases, wherein the recycle stream comprises propane, butane, or a combination thereof, and the light gases comprise methane and hydrogen.

4. The method of claim 1, wherein the catalyst particles are fluidized inside each of the reactors.

5. The method of claim 1, wherein the catalyst particles are 10-500 micrometers in diameter.

6. The method of claim 1, wherein, in the converting step, an outside wall of each of the reactors is heated by a flue gas, wherein the flue gas is generated by combustion of fuel.

7. The method of claim 1, wherein a pressure of the reactor is 100 psig (790 kPa) or less during the converting step.

8. The method of claim 1, wherein a temperature of the catalyst particles is between 500° C. and 700° C. during the converting step.

9. The method of claim 1, wherein a temperature of the furnace is between 700° C. and 1200° C. during the converting step.

10. The method of claim 1, wherein the upper end portion is 10%-70% of the length of each of the reactors in a height direction.

11. The method of claim 1, wherein, in the regeneration mode, all the reactors in the furnace are fluidly disconnected from the light alkane feed and fed with a gas stream for catalyst regeneration.

12. The method of claim 1, wherein the reactors are connected in parallel, but not in series.

13. The method of claim 1, wherein the furnace comprises multiple furnaces and the first merged effluent stream from each of the multiple furnaces is further merged with each other to form a second merged effluent stream.

14. The method of claim 13, wherein the reactors in the furnace in which the regenerating occurs are fluidly disconnected from the light alkane feed and fed with a gas stream for catalyst regeneration.

15. The method of claim 14, wherein the reactors in the furnace in which the regenerating occurs are fluidly disconnected from the second merged effluent stream.

\* \* \* \* \*